United States Patent
Takagi et al.

(10) Patent No.: US 8,135,203 B2
(45) Date of Patent: Mar. 13, 2012

(54) CELL IMAGE PROCESSOR AND CELL IMAGE PROCESSING METHOD

(75) Inventors: Kosuke Takagi, Saitama (JP); Yuichiro Matsuo, Tokyo (JP); Yoshihiro Shimada, Kanagawa (JP)

(73) Assignee: Olympus Corporation, Tokyo (JP)

( * ) Notice: Subject to any disclaimer, the term of this patent is extended or adjusted under 35 U.S.C. 154(b) by 474 days.

(21) Appl. No.: 12/439,778

(22) PCT Filed: Aug. 24, 2007

(86) PCT No.: PCT/JP2007/066415
§ 371 (c)(1),
(2), (4) Date: Mar. 3, 2009

(87) PCT Pub. No.: WO2008/029635
PCT Pub. Date: Mar. 13, 2008

(65) Prior Publication Data
US 2009/0324050 A1     Dec. 31, 2009

(30) Foreign Application Priority Data
Sep. 6, 2006   (JP) ................................. 2006-241312

(51) Int. Cl.
*G06K 9/00* (2006.01)
(52) U.S. Cl. ........................................ 382/133; 382/128
(58) Field of Classification Search ........... 382/128–134
See application file for complete search history.

(56) References Cited

U.S. PATENT DOCUMENTS 5,408,307 A  *  4/1995  Yamamoto et al. ............. 356/73

FOREIGN PATENT DOCUMENTS

| JP | 02-055953   | 2/1990  |
|----|-------------|---------|
| JP | 10-090163   | 4/1998  |
| JP | 11-248698   | 9/1999  |
| JP | 2000-180347 | 6/2000  |
| JP | 2001-307066 | 11/2001 |

* cited by examiner

*Primary Examiner* — David Mis
(74) *Attorney, Agent, or Firm* — Scully, Scott, Murphy & Presser, P.C.

(57) ABSTRACT

Cells showing specific characters can be separated from noise, extracted, and analyzed, through processing of a cell image. It is intended to provide a cell image processor (1) comprising: a characteristic quantity measuring section (11) which processes a cell image obtained by photographing cells to measure characteristic quantities of respective cells in the cell image; a characteristic quantity distribution forming section (12) which forms the distribution of the thus measured characteristic quantities; a group forming section (13) which divides cells having continuously distributed characteristic quantities into groups in the thus formed characteristic quantity distribution; and a specific cell extracting section (14) which extracts cells having characteristic quantities falling within a predetermined range at both ends of a characteristic quantity distribution in each group, as specific cells.

7 Claims, 5 Drawing Sheets

LONG CELL → LARGE PARAMETER

ROUNDED CELL → SMALL PARAMETER

CELL IMAGE PROCESSOR AND CELL IMAGE PROCESSING METHOD

TECHNICAL FIELD

The present invention relates to a cell image processor and a cell image processing method.

BACKGROUND ART

Conventionally, a cell image analyzer which performs image processing so as to analyze a cell image has been known (for example, refer to Patent Document 1).

This apparatus is to perform highly accurate analytical processing through elimination of the effect of noise when extracting characteristics in the cell image.

Patent Document 1:

Japanese Unexamined Patent Application, Publication No. 2001-307066

DISCLOSURE OF INVENTION

When characteristics of cells are to be extracted with an automatic cell image processor through processing of large amounts of data in a short time, cells having specific characteristic quantities are regarded as noise to be eliminated from the target of processing.

For example, in an analysis to measure how the cell size is changed by a drug, a comparison is made between the size of a cell group without administration of the drug and the size of a cell group cultured with administration of the drug; in which case, the comparison is between their average sizes, and cells out of the average sizes are eliminated from the target of comparison.

For this reason, cells showing specific phenomena differing from the trend of the majority of cells end up being buried without analysis. However, some specific phenomena are meaningful and it is necessary to enable extraction and analysis of such cells.

In addition, specific phenomena differing from the trend of the majority of cells are difficult to distinguish from noise such as a contingently occurring dirt. Accordingly, it is necessary to separate specific cells from noise and to extract such cells.

The present invention takes the above situation into consideration with an object of providing a cell image processor and a cell image processing method by which cells showing specific characters can be separated from noise, extracted, and analyzed, through processing of a cell image.

In order to achieve the above object, the present invention provides the following solutions.

A first aspect of the present invention is a cell image processor comprising: a characteristic quantity measuring section which processes a cell image obtained by photographing cells to measure characteristic quantities of respective cells in the cell image; a characteristic quantity distribution forming section which forms the distribution of the thus measured characteristic quantities; and a specific cell extracting section which extracts cells having continuously distributed characteristic quantities in the thus formed characteristic quantity distribution, as specific cells.

According to the first aspect mentioned above, a cell image obtained by photographing cells is processed to measure characteristic quantities of respective cells in the cell image by the operation of the characteristic quantity measuring section, and the distribution of the characteristic quantities that have been measured by the characteristic quantity measuring section is formed by the operation of the characteristic quantity distribution forming section. In this state, cells having continuously distributed characteristic quantities are extracted as specific cells by the operation of the specific cell extracting section.

That is to say, when large amounts of data are to be processed to analyze characters of cells, usually, it is rare for a single cell to have a one-off specific characteristic quantity, but there exist a plurality of cells having similar specific characteristic quantities. This means that the characteristic quantity distribution is continuously distributed being centered at one or more peak(s). Accordingly, cells having continuously distributed characteristic quantities can be extracted as specific cells.

In the above first aspect, the specific cell extracting section may also exclude cells having discontinuously distributed characteristic quantities.

As described above, since characteristic quantities of normal cells are continuously distributed, exclusion of cells having discontinuously distributed characteristic quantities enables efficient exclusion of noise without exclusion of specific cells.

In addition, in the above first aspect, the characteristic quantity measuring section may also measure a plurality of types of characteristic quantities of respective cells, and the characteristic quantity distribution forming section may also form the characteristic quantity distribution in correlation with the plurality of types of characteristic quantities.

By so doing, those specific with respect to a plurality of types of characteristic quantities can be excluded as noise.

In the above first aspect, the setting of a predetermined range of the specific cell extracting section may be changeable.

By so doing, the degree of the specificity of specific cells to be extracted can be adjusted by changing the setting of the predetermined range.

In the above first aspect, there may also be provided a display unit which divides cells having continuously distributed characteristic quantities into groups in the characteristic quantity distribution that has been formed by the characteristic quantity distribution forming section, and displays them respectively by groups.

By so doing, it becomes possible for researchers to visually observe images of cells respectively by groups including thus extracted specific cells, which enables verification by the researchers.

A second aspect of the present invention is a cell image processing method comprising: a measuring step for processing a cell image obtained by photographing cells to measure characteristic quantities of respective cells in the cell image; a distribution forming step for forming the distribution of the thus measured characteristic quantities; and an extracting step for extracting cells having continuously distributed characteristic quantities in the thus formed characteristic quantity distribution, as specific cells.

In the above second aspect, the extracting step may also serve to exclude cells having discontinuously distributed characteristic quantities.

According to the present invention, an effect is provided in which cells showing specific characters can be separated from noise, extracted, and analyzed, through processing of a cell image.

EXPLANATION OF REFERENCE SIGNS

Figure 1:
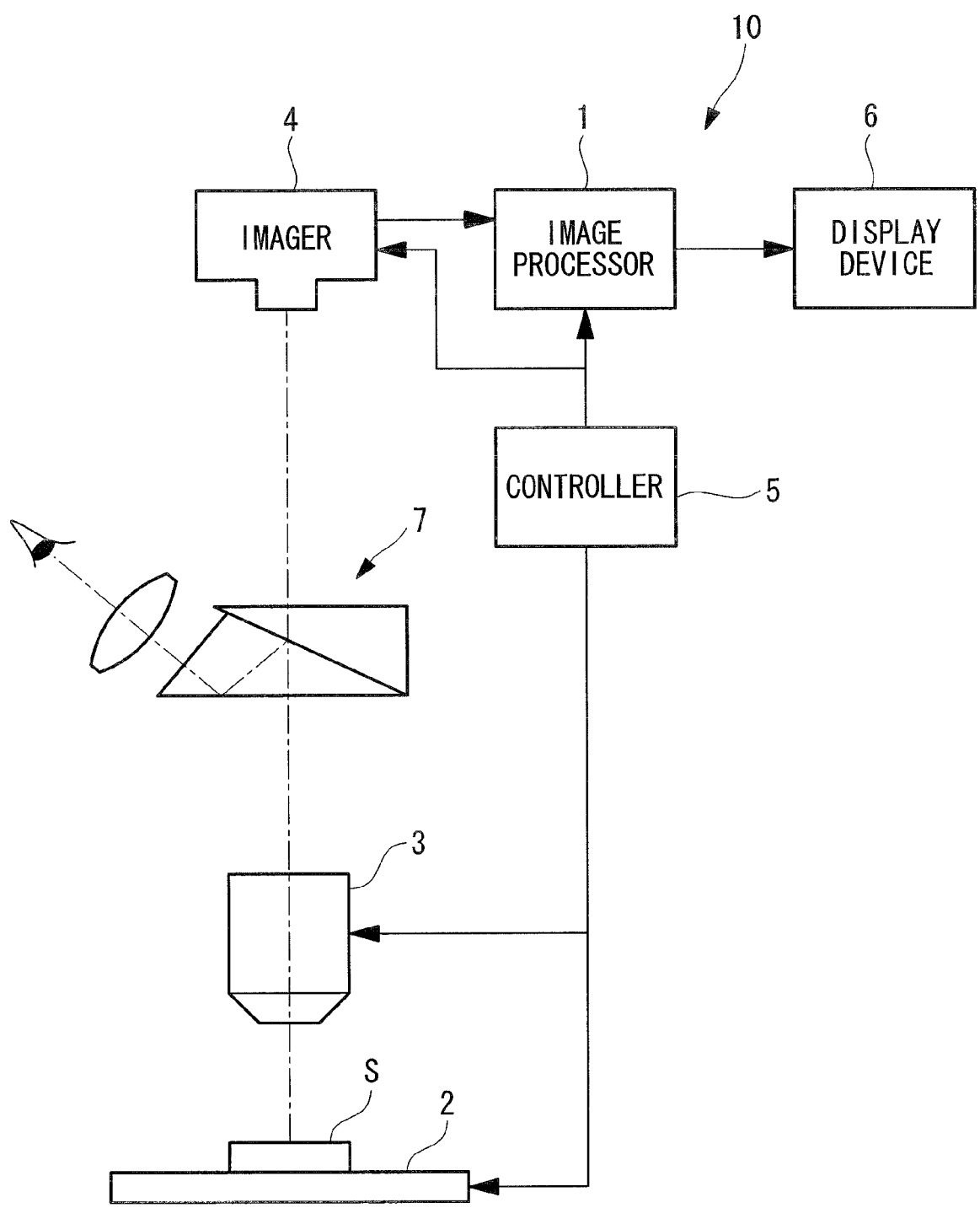
FIG. 1 is an overall schematic structural diagram showing an analyzer equipped with a cell image processor according to one embodiment of the present invention.

S: Cell sample
1: Cell image processor
6: Display device (Display unit)
11: Characteristic quantity measuring section
12: Distribution forming section (Characteristic quantity distribution forming section)
13: Group forming section
14: Specific cell extracting section

BEST MODE FOR CARRYING OUT THE INVENTION

Hereunder is a description of a cell image processor 1 and a cell image processing method according to one embodiment of the present invention, with reference to FIG. 1 to FIG. 6B.

The cell image processor 1 according to this embodiment is installed in an analyzer 10 shown in FIG. 1. The analyzer 10 comprises: a stage 2 for placing a cell sample S or the like thereon and moving it in two horizontal axial directions; an objective lens 3 for collecting fluorescence from the cell sample S; an imager 4 such as a CCD camera, for photographing the fluorescence collected by the objective lens 3; the cell image processor 1 which processes the image obtained by the imager 4; a controller 5 which controls these devices; and a display device 6 which displays the cell image processed by the cell image processor 1. In the diagram, the reference symbol 7 denotes an ocular optical system for visually observing the cell sample S, either as it is or in the form of collected fluorescence from the cell sample S, through the objective lens 3.

It is designed such that the cell sample S or the like is placed on a slide glass or a multiplate.

Figure 2:
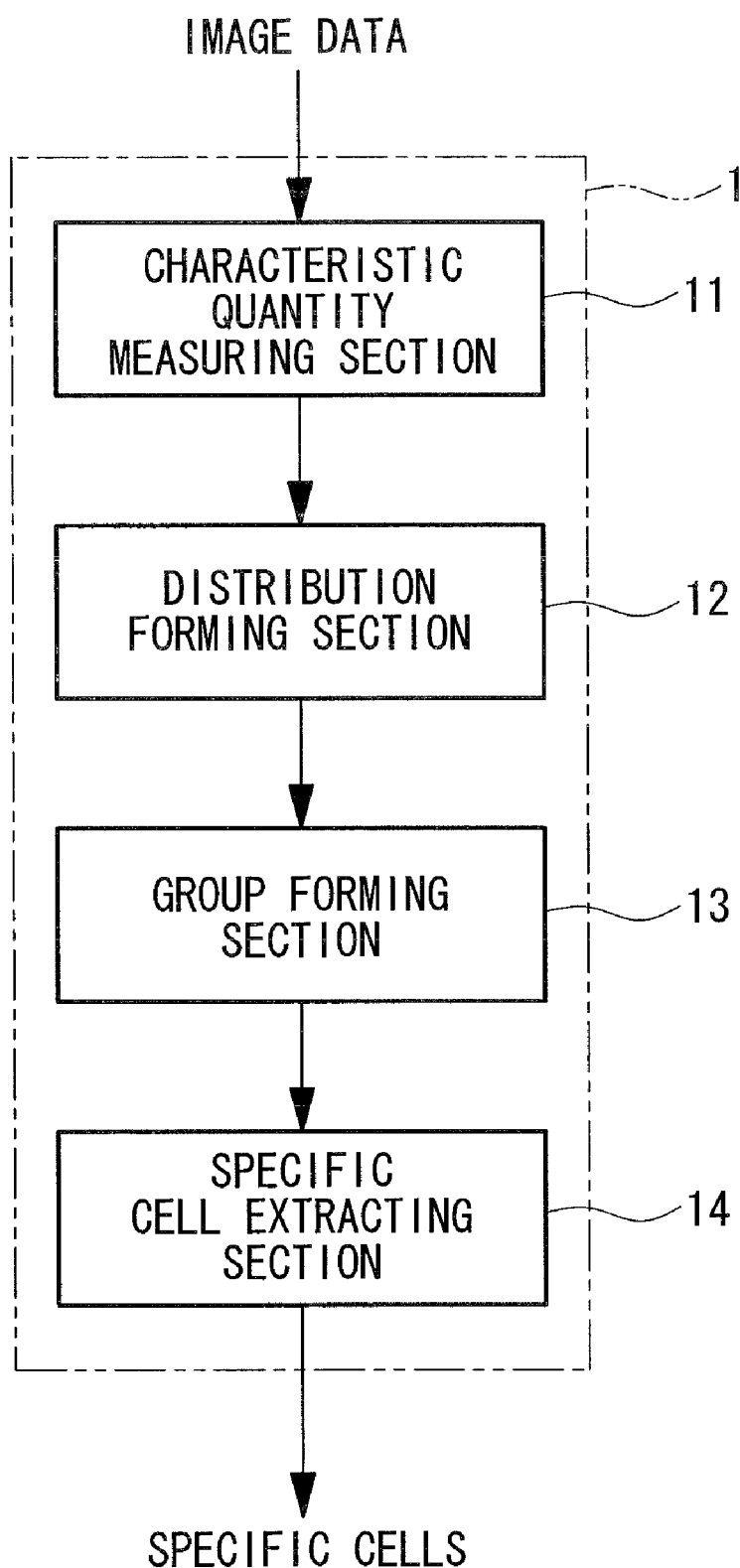
FIG. 2 is a block diagram showing the cell image processor according to this embodiment equipped in the analyzer of FIG. 1.

As shown in FIG. 2, the cell image processor 1 according to this embodiment comprises: a characteristic quantity measuring section 11 which processes the image data obtained by the imager 4 to measure characteristic quantities of respective cells; a distribution forming section 12 which forms the distribution thereof based on the thus measured characteristic quantities; a group forming section 13 which divides the thus formed characteristic quantity distribution into groups; and a specific cell extracting section 14 which extracts cells having characteristic quantities falling within a predetermined range at both ends of a characteristic quantity distribution respectively by grouped cells or by each group thus formed, as specific cells.

As to the "characteristic quantity", for example, morphological characters of cells, and luminance of cells can be enumerated. The morphological character of cells includes, for example, the area, the perimeter, and the mean curvature of cells. The characteristic quantity measuring section 11 is designed to measure such morphological character(s) of cells, for example, through binarization of a cell image to obtain profile images of cells. It is also designed to measure the luminance of cells on the basis of luminance values of pixels that form the images of respective cells.

The term "specific cell" means a cell which is largely out of the mean value and the distribution, a cell which belongs to a small group as a result of the grouping process, a cell which has a specific parameter correlation, or the like.

Figure 3A:
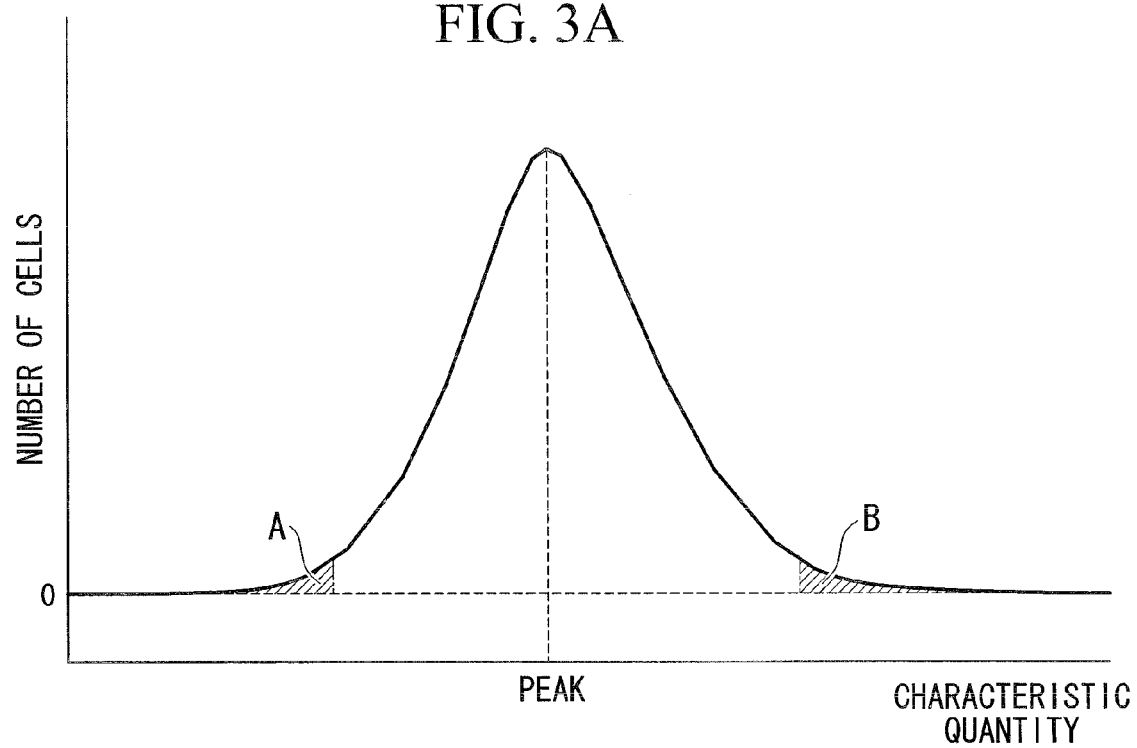
FIG. 3A is a graph showing an example of a characteristic quantity distribution formed by the cell image processor of FIG. 1.
Figure 3B:
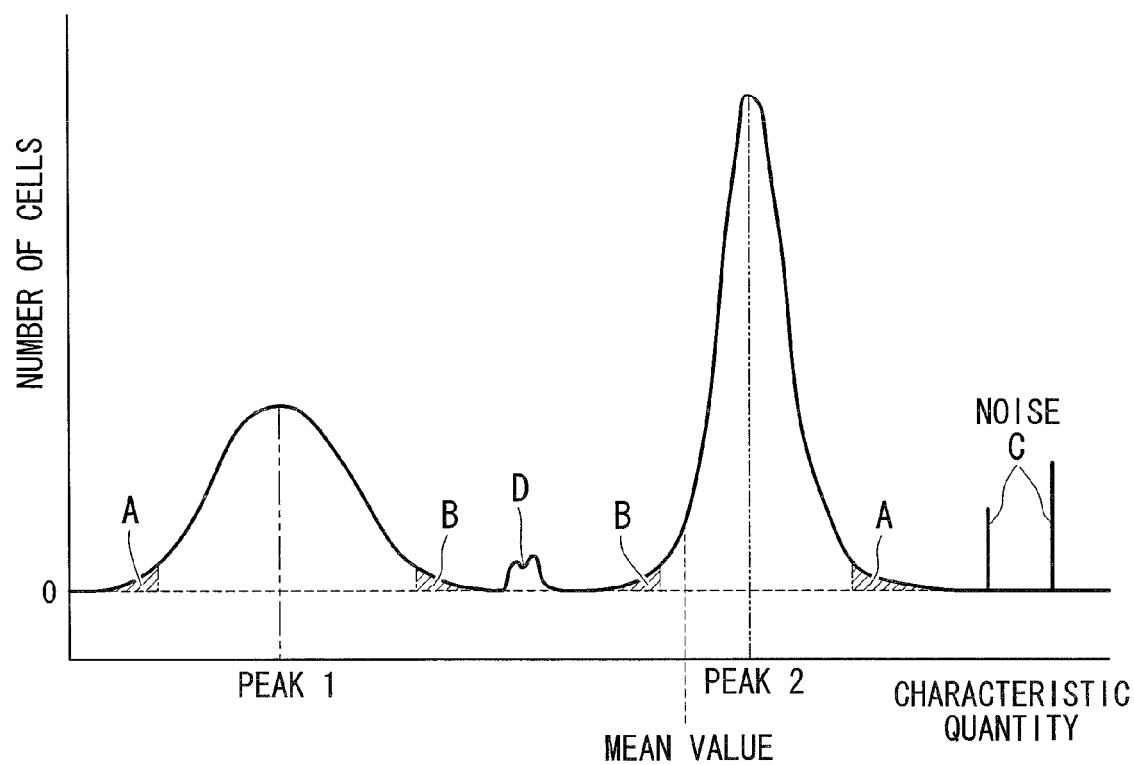
FIG. 3B is a graph showing another example of a characteristic quantity distribution formed by the cell image processor of FIG. 1.

The distribution forming section 12 is to form the distribution of cells with respect to the characteristic quantities, for example as shown in FIG. 3A and FIG. 3B, by taking the characteristic quantity as the x-axis, and the number of cells as the y-axis. FIG. 3A shows a characteristic quantity distribution being a normal distribution in a case where the characteristic quantity of cells has a simple statistical feature. On the other hand, in a case where the statistical feature becomes more complicated, the distribution has a plurality of peaks. In the case of FIG. 3B, two large peaks are shown.

The group forming section 13 is to obtain the characteristic quantity of each peak so as to calculate the mean value and the distribution of the characteristic quantities of cells existing around the corresponding peak, respectively by each peak. By so doing, the characteristic quantity distribution can be divided into groups.

Moreover, the specific cell extracting section 14 is to extract cells falling within, for example, a range of 5% at both ends of a distribution in the characteristic quantity distribution that has been divided into groups, in cases of normal distribution as shown in FIG. 3A (hatched areas A and B in FIG. 3A).

In a case where a group D of small peak is present in addition to two large peaks as shown in FIG. 3B, the specific cell extracting section 14 acts to extract this group D by regarding them as specific cells. At this time, the hatched areas A and B may also be extracted as specific cells.

That is to say, according to the cell image processor 1 of this embodiment, it becomes possible to extract cells falling within a range of 5% at both ends of a distribution in the characteristic quantity distribution having one or more continuously distributed group(s), and to extract cells in a group having a very small peak as compared to other peaks.

Hereunder is a description of the image processing method with the thus configured cell image processor 1 according to this embodiment.

In order to extract specific cells with use of the cell image processor 1 according to this embodiment: firstly, the cell sample S placed on a slide glass or a multiplate is mounted on the stage 2; then the cell sample S is horizontally moved by moving the stage 2; and the image of the cell sample S is obtained by the imager 4 while focusing on the cell sample S by moving the objective lens 3.

Then, the obtained cell image is processed to measure characteristic quantities of respective cells in the cell image; the distribution of the thus measured characteristic quantities is formed; and cells having continuously distributed characteristic quantities are divided into groups in the thus formed characteristic quantity distribution.

When large amounts of data are to be processed to analyze characters of cells, usually, it is rare for a single cell to have a one-off specific characteristic quantity, but there exist a plurality of cells having similar specific characteristic quantities. This means that the characteristic quantity distribution is continuously distributed being centered at one or more peak (s).

Therefore, by dividing cells having continuously distributed characteristic quantities into groups, noise having a one-off specific characteristic quantity as shown by the reference symbol C in FIG. 3B can be excluded from the target of analysis. In each group, the characteristic quantities are continuously distributed being centered at each peak. Thus, it becomes possible to extract cells having characteristic quantities falling within a predetermined range, for example, 5% at both ends of the distribution, as specific cells, and to extract a group smaller than other groups as specific cells.

If cells having specific characteristic quantities are to be extracted without the grouping process, it is difficult to extract specific cells falling in the vicinity of the overall mean value as shown by the reference symbol D in FIG. 3B. On the other hand, by dividing cells having continuously distributed characteristic quantities into groups, like the cell image processor 1 according to this embodiment does, it becomes possible to extract cells existing in the region of the reference symbol D, as cells having specific characteristic quantities.

This embodiment is designed such that the distribution of cells is formed with respect to a single type of characteristic quantity to extract cells having specific characteristic quantities; however, instead of this, two or more types of characteristic quantities may also be used to form a distribution. In this case, the arrangement may also be such that a single parameter is calculated using such two or more types of characteristic quantities so as to form the distribution with respect to the single parameter.

Figure 6A:
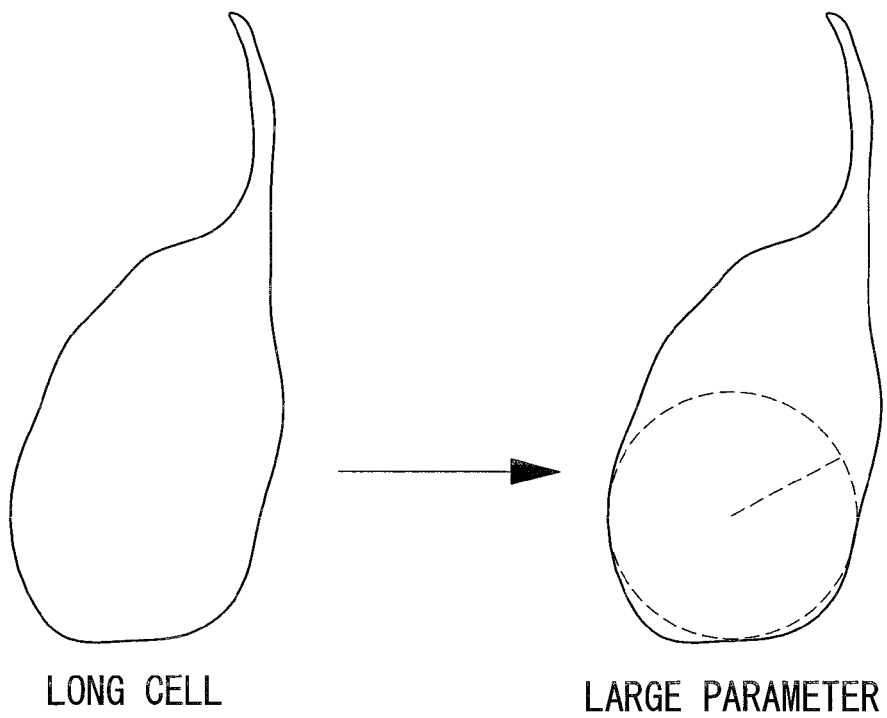
FIG. 6A illustrates an example of a morphological parameter for use in grouping process with the cell image processor of FIG. 1.
Figure 6B:
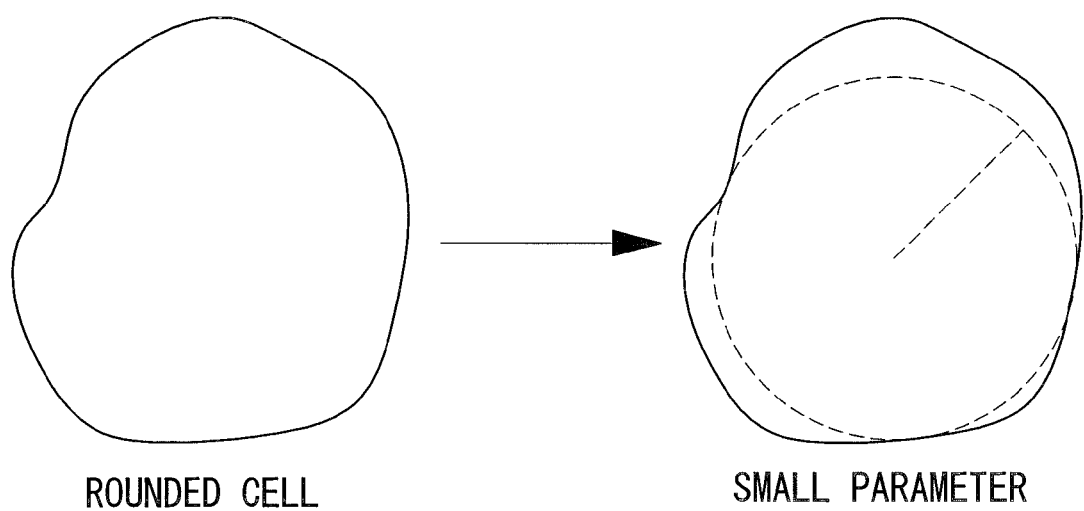
FIG. 6B illustrates an example of another morphological parameter for use in grouping process with the cell image processor of FIG. 1.

For example, as shown in FIG. 6A and FIG. 6B, the size of a nerve cell is expressed by the radius of an inscribed circle touching the profile of the cell body of the nerve cell, and the length of the thin projecting part of the nerve cell is expressed by the perimeter of the profile. Then, the perimeter is normalized by the radius of the inscribed circle. By so doing, a new single parameter (perimeter/radius of inscribed circle) can be obtained. For example, if the cell is wholly rounded and there is no extending projection found, then the parameter can be expressed as 1; while if the projection is long enough, then the parameter can be expressed as 2.5. Specific cells may also be extracted on the basis of this value.

As the standard model, a highly active nerve cell is big in size and long in length of the thin projecting part, while a low active nerve cell is small in size and short in length of the thin projecting part. Accordingly, by obtaining the distribution on the parameter basis, specific ones nonconforming to the standard model, for example, those being big in size but short in length of the thin projecting part and those being small in size but long in length of the thin projecting part can be extracted as specific cells.

Figure 4:
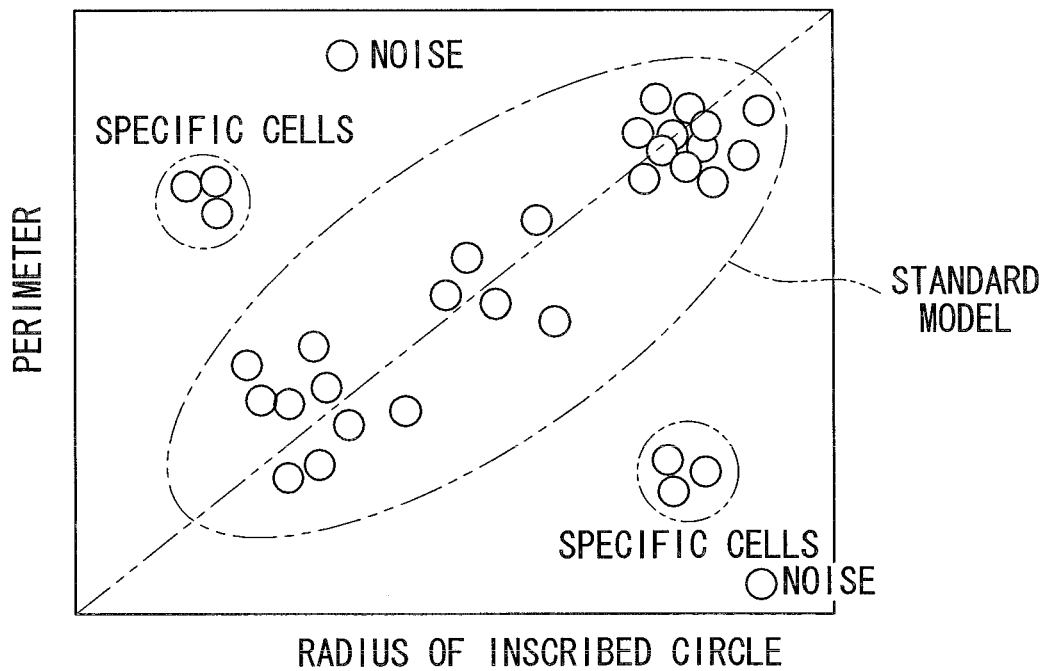
FIG. 4 is a graph showing an example of a two-dimensional distribution with respect to two types of characteristic quantities formed by the cell image processor of FIG. 1.

Even if the distribution is formed with use of two or more types of characteristic quantities, a specific cell existing alone can be extracted as noise (FIG. 4). In other words, it is a feature of noise to be distinctive with respect to a plurality of types of characteristic quantities. Specifically speaking, a tiny dirt in a culture container or the like is very small in size and highly luminous. In addition, this appears as a one-off phenomenon in the distribution. On the other hand, although normal cells tend to get small in size and highly luminous in the death process, they often retain a certain degree of size. Accordingly, those very small in size and highly luminous can be eliminated as noise such as a dirt.

Figure 5:
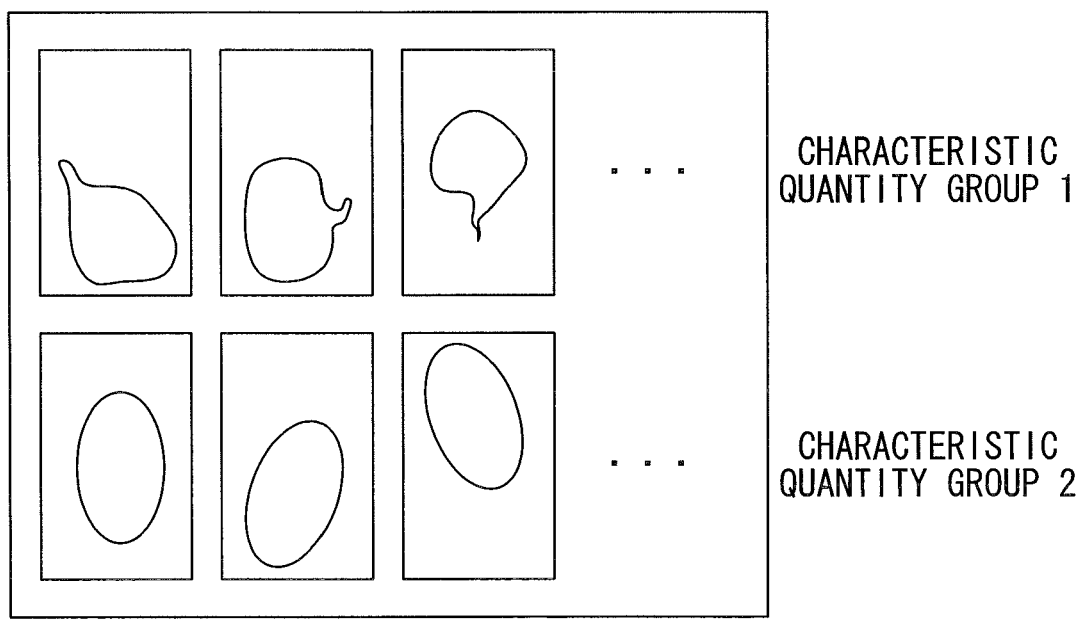
FIG. 5 illustrates a display example which displays cells respectively by groups of characteristic quantities that have been grouped by the cell image processor of FIG. 1.

In this embodiment, as described above, characteristic cells are extracted by dividing the formed characteristic quantity distribution into groups. Therefore, the arrangement may also be such that images of the extracted respective cells are aligned respectively by groups as shown in FIG. 5, or collectively displayed by each group. In addition, the arrangement may also be such that characteristic cells are displayed in alignment either as images including surrounding areas, or images of cells alone excluding such surrounding areas as shown in FIG. 5, so that the selection of the image by the observer leads to display data of the characteristic quantity of the selected characteristic cell or areas around the cell.

By so doing, grouped cells having a common character can be displayed in a comparable manner, for the observer, which provides an advantage of facilitating the final judgment by the observer through visual observation.

Generally, specific phenomenon is not only caused by a one-off causative factor, but also induced by several composite factors. Therefore, the arrangement may also be such that cells extracted and displayed as specific cells are further classified by predetermined factors and displayed in alignment by each classification.

For example, for observing a reaction in which an intracellular receptor is expressed in response to a certain type of hormone, the expression of the receptor can be observed by, for example, introducing a fluorescent protein gene.

Here, the magnitude of the reaction can be quantified by the level of expressed fluorescent protein, that is to say, the level of fluorescence (luminance) when respective cells are observed with a fluorescence microscope. Therefore, it is effective to classify "cells showing low fluorescence level" as specific cells, and to classify these cells in terms of the "DNA level" as an associated factor with cell cycles.

If the observer frames a hypothesis that "small cells are considered to be weakened and dying, in which case, the reaction process of such cells must be no longer functioning", then the verification of the hypothesis by the observer can be supported by displaying data of classification in terms of the size with respect to cells showing low fluorescence level that have been extracted as specific cells.

The user-friendliness can be improved by classification of the thus extracted respective cells in terms of such a morphological parameter so as to classify them into several characteristic cell groups, followed by display of these cells respectively by groups using the image displaying method likewise of FIG. 5.

The invention claimed is:

1. A cell image processor comprising:
    a characteristic quantity measuring section which processes a cell image obtained by photographing cells to measure characteristic quantities of respective cells in the cell image;
    a characteristic quantity distribution forming section which forms the distribution of the thus measured characteristic quantities;
    a group forming detecting section that detects the characteristic quantity at one or more peaks from the distribution of the characteristic quantity formed by the characteristic quantity distribution forming section; and
    a specific cell extracting section which extracts cells having continuously distributed characteristic quantities being centered at one or more peaks in the thus formed characteristic quantity distribution, as specific cells.

2. A cell image processor according to claim 1, wherein said specific cell extracting section excludes cells having discontinuously distributed characteristic quantities.

3. A cell image processor according to claim 1, wherein
said characteristic quantity measuring section measures a plurality of types of characteristic quantities of respective cells, and
said characteristic quantity distribution forming section forms a characteristic quantity distribution in correlation with the plurality of types of characteristic quantities.

4. A cell image processor according to claim 1, wherein a setting of an extracted range of said specific cell extracting section is changeable.

5. A cell image processor according to claim 1, comprising a display unit which divides cells having continuously distributed characteristic quantities into groups in the characteristic quantity distribution that has been formed by said characteristic quantity distribution forming section, and displays them respectively by groups.

6. A cell image processing method comprising:
a measuring step for processing a cell image obtained by photographing cells to measure characteristic quantities of respective cells in the cell image;
a distribution forming step for forming the distribution of the thus measured characteristic quantities;
a group forming step for detecting the characteristic quantity at one or more peaks from the distribution of the characteristic quantity formed by the characteristic quantity distribution forming section; and
an extracting step for extracting cells having continuously distributed characteristic quantities being centered at one or more peaks in the thus formed characteristic quantity distribution, as specific cells.

7. A cell image processing method according to claim 6, wherein said extracting step is to exclude cells having discontinuously distributed characteristic quantities.

* * * * *